US006686344B1

(12) United States Patent
Uckun

(10) Patent No.: US 6,686,344 B1
(45) Date of Patent: Feb. 3, 2004

(54) ORGANIC-ARSONIC COMPOUNDS

(75) Inventor: Fatih M. Uckun, White Bear Lake, MN (US)

(73) Assignee: Paker Hughes Institute, St. Paul, MN (US)

( * ) Notice: Subject to any disclaimer, the term of this patent is extended or adjusted under 35 U.S.C. 154(b) by 0 days.

(21) Appl. No.: 10/356,673

(22) Filed: Jan. 30, 2003

(51) Int. Cl.[7] .................... A61K 31/517; A61K 31/655; C07D 239/74; C07D 239/26
(52) U.S. Cl. ...................... 514/150; 514/184; 514/186; 534/694; 544/226
(58) Field of Search .................. 534/694; 544/226; 514/150, 184, 186

(56) References Cited

U.S. PATENT DOCUMENTS

| | | | | |
|---|---|---|---|---|
| 2,415,556 A | * | 2/1947 | Friedheim | 544/181 |
| 3,017,380 A | | 1/1962 | D'Alelio | 525/517 |
| 5,281,588 A | | 1/1994 | Maes et al. | 514/184 |
| 5,635,499 A | | 6/1997 | Floc'h et al. | 514/184 |
| 6,191,123 B1 | | 2/2001 | Uckun et al. | 514/150 |
| 6,482,815 B1 | | 11/2002 | Uckun et al. | 514/184 |
| 6,482,816 B1 | | 11/2002 | Uckun et al. | 514/184 |

FOREIGN PATENT DOCUMENTS

WO     WO 96/16664     6/1996

OTHER PUBLICATIONS

Andres, R. et al., "The Synthesis of Arsonoanilinopyrimidines," *The Journal of the American Chemical Society*, Vol. 67, pp. 946–947 (Jun. 1975).

Calvo, A. et al., "Lung Cancer: Therapeutic Options for Stage IV and Recurrent NSCLC," *Thoracic Oncology*, vol. 105, pp. 189–227 (2001).

Chen, G. et al., "In Vitro Studies on Cellular and Molecular Mechanisms of Arsenic Trioxide ($As_2O_3$) in the Treatment of Acute Promyelocytic Leukemia: $As_2O_3$ Induces $NB_4$ Cell Apoptosis With Downregulation of Bcl–2 Expression and Modulation of PML–RARα/PML Proteins," *Blood*, vol. 88, No. 3, pp. 1052–1061 (Aug. 1, 1996).

D'Cruz, O. et al., "Apoptosis–inducing oxovanadium(IV) complexes of 1, 10–phenanthroline against human ovarian cancer," *Anti–Cancer Drugs*, vol. 11, No. 10, pp. 849–858 (Nov. 2000).

Dai, J. et al., "Malignant Cells Can Be Sensitized to Undergo Growth Inihibition and Apoptosis by Arsenic Trioxide Through Modulation of the Glutathione Redox System," *Blood*, vol. 93, No. 1, pp. 268–277 (Jan. 1, 1999).

Gavrieli, Y., "Identification of programmed cell death in situ via specific labeling of nuclear DNA fragmentation," *J. Cell. Biol.*, vol. 119, No. 3, pp. 493–501 (Nov. 1992).

Gill, B., "Chemotherapeutic susceptibility of Trypanosoma evansi to some arsenicals and suramin–tryparsamid complex," *Indian Vet. Res. Inst., Izatnagar, India, Acta Vet. (Brno)*, vol. 40, No. 2, 1 pg. (Abstract only) (1971).

Green, J. et al., "Survival and recurrence after concomitant chemotherapy and radiotherapy for cancer of the uterine cervix: a systematic review and meta–analysis," *The Lancet*, vol. 358, No. 9284, pp. 781–786, (Sep. 8, 2001).

Greenlee, R. et al., "Cancer Statistics, 2000," *CA—A Cancer Journal for Clinicians*, vol. 50, No. 1, pp. 7–33, (Jan./Feb. 2000).

Jing, Y. et al., "Arsenic Trioxide Selectively Induces Acute Promyelocytic Leukemia Cell Apoptosis Via a Hydrogen Peroxide–Dependent Pathway," *Blood*, vol 94, No. 6, pp. 2102–2111 (Sep. 15, 1999).

Liu, X. et al., "Organic Phenyl Arsonic Acid Compounds with Potent Antileukemic Activity," *Biorganic & Medinical Chemistry Letters*, vol. 13, pp. 581–583 (2003).

"Mineral Tolerance of Domestic Animals," *National Academy of Sciences*, p. iii and pp. 40–53 (1980).

"Mortality Patterns–United States, 1997," *MMWR*, vol. 48, No. 30, pp. 664–668 (Aug. 6, 1999).

Nomoto. Y. et al., "Studies on Cardiotonic Agents. I. Synthesis of Some Quinazoline Derivatives," *Chemical & Pharmaceutical Bulletin*, vol. 38, No. 6, pp. 1591–1595 (1990).

Recht, A., "Postmastectomy Locoregional Radiotherapy: Is It Here to Stay?" *Seminars in Oncology*, vol. 28, No. 3, pp. 245–252 (Jun. 2001).

Shen, Z. et al., "Use of Arsenic Trioxide ($As_2O_3$) in the Treatment of Acute Promyelocytic Leukemia (APL): II. Clinical Efficacy and Pharmacokinetics in Relapsed Patients," *Blood*, vol. 89, No. 9, pp. 3354–3360, (May 1, 1997.).

Simone, J., "Oncology," *Cecil Textbook of Medicine*, 20th Ed., vol. 1, Part XIV, pp. 1004–1010 (date unknown).

Soignet, S. et al., "Complete Remission After Treatment of Acute Promyelocytic Leukemia with Arsenic Trioxide," *The New England Journal of Medicine*, vol. 339, No. 19, pp. 1341–1348 (Nov. 5, 1998).

Takatsuka, Y. et al., "Various analogs of anthranilic acid and their anti–cancer effects," *Mie Med. J.*, vol. 17. No. 1, pp. 83–92 (Abstract only) (1967).

"Trypanocidal activity of some pyrimidylaminophenylarsonic compounds," *Chemical Abstracts*, vol. 53, No. 11 pp. 10243–10346 (Jun. 10, 1959).

Uckun, F. et al., "Biotherapy of B–Cell Precursor Leukemia by Targeting Genistein to CD19–Associated Tyrosine Kinases," *Science*, vol. 267, pp. 886–891 (Feb. 10, 1995).

(List continued on next page.)

*Primary Examiner*—Fiona T. Powers
(74) *Attorney, Agent, or Firm*—Merchant & Gould P.C.

(57) ABSTRACT

Novel organic arsonic compounds are described as tumor inhibiting, and cancer treating compounds. Methods and compositions for inhibiting tumor cells and treating cancer are also provided.

17 Claims, No Drawings

OTHER PUBLICATIONS

Waurzyniak, B. et al., In Vivo Toxicity, Pharmacokinetics, and Antileukemic Activity of TXU (Anti–CD7)–Pokeweed Antiviral Protein Immunotoxin, *Clinical Cancer Research*, vol. 3, pp. 881–890 (Jun. 1997).

Weinstein, S., "Integrating Palliative Care in Oncology," *Cancer Control*, vol. 8, No. 1, pp. 32–35, (Jan./Feb. 2001).

Yuki, H. et al., "Synthesis of Purine and Pyrimidine Derivatives of Arsonic Acid," *Chemical & Pharmaceutical Bulletin*, vol. 15, No. 7, pp. 1052–1055 (Jul. 1967).

Zhu, D. et al., "Calphostin C Triggers Calcium–dependent Apoptosis in Human Acute Lymphoblastic Leukemia Cells," *Clinical Cancer Research*, vol. 4, No. 12, pp. 2967–2975 (Dec. 1998).

Zhu, X. et al., "Apoptosis and Growth Inhibition in Malignant Lymphocytes after Treatment with Arsenic Trioxide at Clinically Achievable Concentrations," *Journal of the National Cancer Institute*, vol. 91, No. 9, pp. 772–778 (May 5, 1999).

* cited by examiner

ORGANIC-ARSONIC COMPOUNDS

BACKGROUND OF THE INVENTION

Cancer is a major disease that continues as one of the leading causes of death at any age. In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

SUMMARY OF THE INVENTION

The invention provides compounds of formula (I)

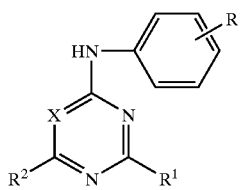

where R is

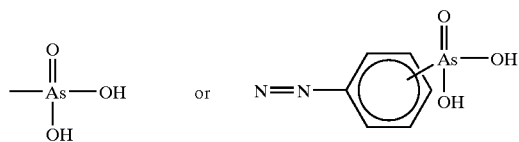

$R^2$ is H, $NR^3R^4$, $SR^3$, $OR^3$, or a group capable of bonding with X, when X is C, to form a fused aromatic or 5- or 6-membered heteroaromatic ring, wherein $R^3$ and $R^4$ are each independently hydrogen or a $C_1$–$C_4$ alkyl group;

or a pharmaceutically acceptable salt thereof.

The invention also provides a compound having the formula (II)

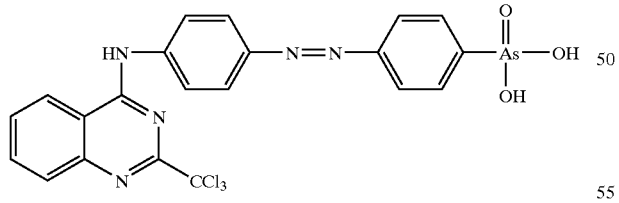

The invention also provides a method of inhibiting the growth of tumor cells in a subject that includes administering to the subject a compound of formula I.

The invention also provides a method of treating cancer that includes administering to a subject a compound of formula I.

DETAILED DESCRIPTION OF THE INVENTION

The present invention provides novel organic arsonic acid substituted compounds having potent activity as cytotoxic agents. The compounds of the invention are useful agents in treating tumor cells, and treating cancer, for example leukemia.

DEFINITIONS

All scientific and technical terms used in this application have meanings commonly used in the art unless otherwise specified. As used in this application, the following words or phrases have the meanings specified.

As used herein, the term "about" applies to all numeric values, whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "halo" or "halogen" is used to describe an atom selected from the group of Bromine (Br), Chlorine (Cl), Fluorine (F) and Iodine (I).

The term "haloalkyl" is used to describe a functional group having an alkyl group that has at least one hydrogen substituted with a halogen.

Compounds of the Invention

The organic arsonic acid substituted compounds of the invention have the general structure represented by formula (I):

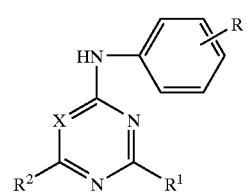

where R is

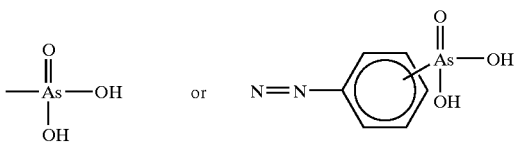

$R^1$ is halo, or haloalkyl. In one embodiment of the invention, $R^1$ is F, Cl, Br, or I. In another embodiment of the invention, $R^1$ is $CH_2X$, $CHX_2$, or $CX_3$, where X is F, Cl, Br, or I. In yet another embodiment of the invention, $R^1$ is $CX_3$, where X is F, Cl, Br, or I. In a further embodiment, $R^1$ is $CCl_3$.

$R^2$ is H, $NR^3R^4$, $SR^3$, $OR^3$, or a group capable of bonding with X, when X is C, to form a fused aromatic or 5- or 6-membered heteroaromatic ring, wherein $R^3$ and $R^4$ are each independently hydrogen or a $C_1$–$C_4$ alkyl group; or a pharmaceutically acceptable salt thereof. In one embodiment of the invention, $R^2$ is a fused aromatic ring. In yet another embodiment of the invention, $R^2$ is a benzene or naphthalene ring, which can be unsubstituted or substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, $SO_2NR^3R^4$ in which $R^3$ and $R^4$ are as defined above, and $SO_2F$. In a further embodiment, $R^2$ is a benzene ring unsubstituted or substituted by one or more groups selected from halo, hydroxy, $C_1$–$C_4$ alkoxy or trifluoromethyl. In yet a further embodiment, $R^2$ is benzene.

One embodiment of the invention is a compound of the formula (II) below.

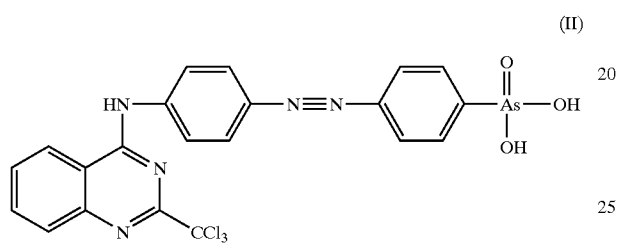

(II)

Salts

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms can be regenerated by treating the salt form with a base. For example, dilute solutions of aqueous base can be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

Synthesis of Compounds of the Invention

The organic arsonic acid substituted compounds of the present invention can be prepared by the condensation of, for example, quinazoline, pyrimidine, triazine or purine derivatives and a organic arsonic acid derivative as shown in Scheme 1. R, $R^1$ and is $R^2$ in Scheme 1 represent the groups previously defined. The reactants, which are either commercially available or prepared by known methods, are heated to reflux in an appropriate solvent for a period of time up to 24 hours. An excess amount of triethylamine is added and the solvent evaporated to afford the crude product which is purified by recrystallization.

Scheme 1

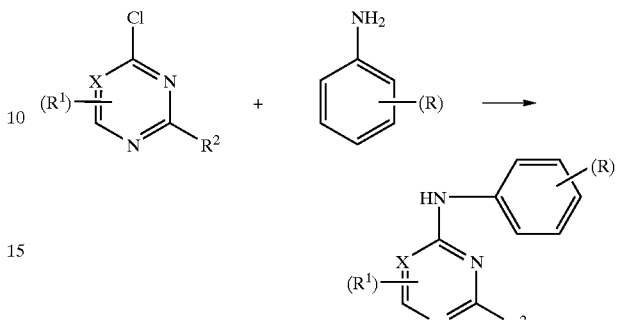

Tumor Treatment

For purposes of this invention, a method of inhibiting the growth of tumor cells includes administering to a subject a compound of the invention in order to achieve an inhibition of tumor cell growth, a killing of tumor cells, reduction of tumor size, induction of cellular apoptosis, and/or increased patient survival time.

The cytotoxic compounds of the invention are suitable for use in mammals. As used herein, "mammals" means any class of higher vertebrates that nourish their young with milk secreted by mammary glands, including, for example, humans, rabbits, and monkeys.

Cancer Treatment

For purposes of this invention, a method of treating cancer includes administering to a subject a compound of the invention in order to inhibit the growth of a cancer cell, kill a cancer cell, reduce the life expectancy of a cancer cell, and/or increase patient survival time.

The compounds of the invention are useful in treating cancers, including but not limited to, leukemia.

Administration Methods

The compounds of the invention can be formulated as pharmaceutical compositions and administered to a mammalian host, including a human patient, in a variety of forms adapted to the chosen route of administration. The compounds are preferably administered in combination with at least one pharmaceutically acceptable carrier, and can be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleageanous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents, and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds can be administered directly to a tumor by tumor injection. In another embodiment of the invention, the compounds can be administered using systemic delivery by intravenous injection.

Solutions or suspensions of the compounds can be prepared in water, isotonic saline (PBS), and optionally mixed with a nontoxic surfactant. Dispersions can also be prepared in glycerol, liquid polyethylene, glycols, DNA, vegetable oils, triacetin and mixtures thereof. Under ordinary conditions of storage and use, these preparations can contain a preservative to prevent the growth of microorganisms.

The pharmaceutical dosage form suitable for injection or infusion use can include sterile, aqueous solutions, dispersions, or sterile powders comprising an active ingredient which are adapted for the extemporaneous preparation of sterile injectable or infusible solutions or dispersions. The final dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols, and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption such as, for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Useful Dose

When used in vivo to kill tumor cells, the administered dose is that effective to have the desired effect, e.g., sufficient to reduce or eliminate tumors. An amount that is effective to have the desired effect is also an amount that is effective to inhibit tumor growth, or treat cancer cells. Appropriate amounts can be determined by those skilled in the art, extrapolating using known methods and relationships, from the in vitro data provided in the Examples.

In general, the dose of the novel organic arsenic acid substituted compounds effective to achieve tumor cell apoptosis, reduction in tumors, and increased survival time, is that which administers micromolar amounts of the compound to the cells, preferably 100 micromolar or greater. The required dose is lessened by conjugation of the compound to a targeting moiety, for example, to preferably 100 nanomolar or greater concentrations.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the organic arsenic acid substituted compounds would be less than for single drug therapy.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

EXAMPLES

The invention may be further clarified by reference to the following Examples, which serve to exemplify some of the embodiments, and not to limit the invention in any way.

Example 1

Synthesis of Substituted Organic Arsonic Compounds

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

The organic arsonic acid substituted compounds of the present invention were prepared by the condensation of quinazoline, pyrimidine, triazine or purine and organic arsonic acid according to the procedure shown in Scheme 1.
Scheme 1

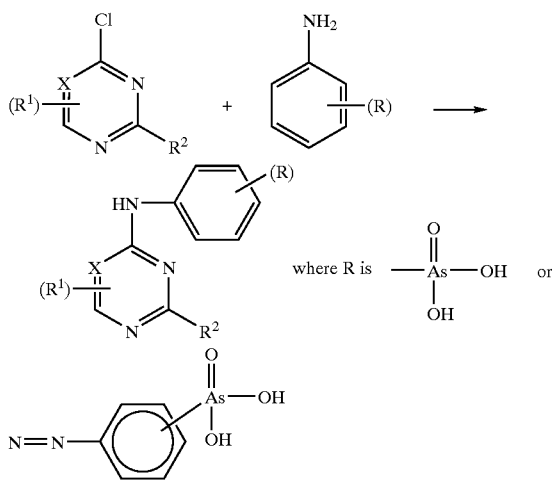

$R^1$ is halo, or haloalkyl.
$R^2$ is H, $NR^3R^4$, $SR^3$, $OR^3$, or a group capable of bonding with X, when X is C, to form a fused aromatic or 5- or 6-membered heteroaromatic ring, wherein $R^3$ and $R^4$ are each independently hydrogen or a $C_1$–$C_4$ alkyl group; or a pharmaceutically acceptable salt thereof.

The reactants, which are either commercially available or prepared by known methods, were chosen as appropriate for the synthesis of the compound desired, and heated to reflux in an appropriate solvent for a period of time up to 24 hours. An excess amount of triethylamine was added and the solvent evaporated to afford the crude product which was purified by recrystallization.

One specific example of synthesis of compound II follows. Compound II was prepared by heating to reflux 2 mmols of 4-chloro-2-trichloromethylquinazoline and 2.2 mmol of 4-(4-aminophenylazo)phenylarsonic acid in the presence of concentrated HCl (2–4 drops) as a catalyst. The mixture was refluxed for 8 to 24 hours.

Example 2

Characterization of Substituted Quinazoline Derivatives

Compound II was synthesized as described above and characterized. The identifying analytical test results are shown below. Proton and carbon Nuclear Magnetic Resonance ($^1H$ and $^{13}C$ NMR) spectra were recorded on a Mercury 2000 Varian spectrometer operating at 300 MHz and 75 MHz, respectively, using an automatic broad band probe. The NMR spectra was recorded in $CDCl_3$ at room temperature. $^1H$ chemical shifts are quoted in parts per million (δ in ppm) downfield from tetramethyl silane (TMS), which was used as an internal standard at 0 ppm and s, d, t, q, m designate singlet, doublet, triplet, quartet and multiplet, respectively. Melting points were determined using a Fisher-Johns melting apparatus and are uncorrected. UV spectra were recorded using a Beckmann Model #DU 7400 UV/V is spectrometer with a cell path length of 1 cm. Methanol was used as the solvent for the UV spectra. Fourier Transform Infrared spectra were recorded using an FT-Nicolet model Protege #460 instrument. The infrared spectra of the liquid samples were run as neat liquids using KBr discs. The KBr pellet method was used for all solid samples. The GC/mass spectrum analysis was conducted using a Hewlett-Packard GC/mass spectrometer model #6890 equipped with a mass ion detector and Chem Station software. The temperature of the oven was steadily increased from 70° C. to 250° C. and the carrier gas was helium.

2-Trichloromethyl-4-4-[4'-(4"-phenylazo)phenylarsonic Acid]-aminoquinazoline

Yield 77$, mp>300° C. $^1H$ NMR (DMSO-$d_6$) δ 10.94 (s, 1H, —NH), 8.45 (d, 2H, $J_{2'',3''}$=9.0 Hz, 2", 6"-H), 8.08–7.77 (m, 4H, 5, 6, 7, 8-H), 7.95 (s, 4H 2', 3', 5', 6'-H), 6.88 (d, 2H, $J_{3'',2''}$=9.0 Hz, 3", 5"-H). $^{13}C$ NMR (DMSO-$d_6$) δ 159.9 (C-2), 158.4 (C-4), 154.7 (C-1'), 154.5 (C-4"), 149.1 (C-4'), 147.7 (C-1"), 132.8 (C-9), 131.7 (C-10), 131.6 (C-2", 6"), 128.6 (C-3'), 128.5 (C-5'), 126.2 (C-6,7), 123.8 (C-5), 123.1 (C-3", 5"), 122.4 (C-2', 6'), 122.2 (C-8), 114.4, 97.9 (C-$CCl_3$). UV (MeOH) $\lambda_{max}$ 205 nm (ε=5407). IR (KBr) $v_{max}$ 3441.6, 3013.3, 2292.2, 1630.7, 1598.2, 1538.6, 1408.4, 1262.0, 1169.9, 1099.4, 817.5 $cm^{-1}$. MS (EI) m/z 565 ($M^+$, 5), 564 ($M^+$ −1, 7), 459 (54), 395 (12), 341 (53), 306 (100). Found: C, 35.59, H, 2.66, N, 9,88. $C_{21}H_{15}AsCl_3$—$N_5O_3$.4HCl requires 3, 33.54, H, 2.68, N, 9.87%.

Example 3

Cytotoxicity of Organic Arsonic Acid Substituted Compounds

The cytotoxicity of compound II was evaluated against two acute lymphoblastic leukemia (ALL) cell lines, NALM-6 (B-lineage ALL), and MOLT-3 (T-lineage ALL) using MTT (3-[4,5-dimethylthiazol-2-yl]-2,5-diphenyl tetrazolium bromide) assay (Boehringer Mannheim Corp., Indianapolis, Ind. The human leukemic cell lines (NALM-6, and MOLT-3) were obtained from the American Type Culture Collection and maintained as a continuous cell line in Dulbecco's modified Eagles's medium supplemented with 10% fetal bovine serum and antibiotics. Briefly, exponentially growing cells were seeded into a 96-well plate at a density of 2.5×$10^4$ cells/well and incubated for 36 hours at 37° C. prior to exposure to the compound. On the day of treatment, culture medium was carefully aspirated from the wells and replaced with fresh medium containing compound II at concentrations ranging from 0.1 to 250 μM. Triplicate wells were used for each treatment.

The cells were incubated with compound II for 24–36 hours at 37° C. in a humidified 5% $CO_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm. To translate the $OD_{540}$ values into the number of live cells in each well, the $OD_{540}$ values were compared to those on standard $OD_{540}$—versus—cell number curves generated for each cell line. The percent survival was calculated using the formula:

$$\% \text{ Survival} = \frac{\text{live cell number [test]}}{\text{live cell number [control]}} \times 100$$

The $IC_{50}$ values for cytotoxic activity were determined using Graph-pad Prism software, version 2.0 (San Diego, Calif., USA) and are shown below in Table 1.

TABLE 1

| Compound | $IC_{50}$(μM) NALM-6 | $IC_{50}$(μM) MOLT-3 |
|---|---|---|
| II | 1.1 ± 0.5 | 2.0 ± 0.8 |

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound of formula (I)

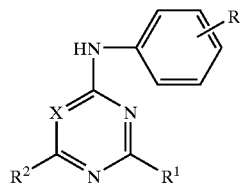

(I)

where R is

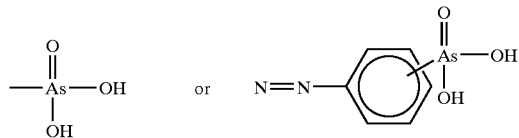

X is C or CH;

$R^1$ is halo, or haloalkyl;

$R^2$ is H, $NR^3R^4$, $SR^3$, $OR^3$ or a group capable of bonding with X, when X is C, to form a fused aromatic or 5- or 6-membered heteroaromatic ring, wherein $R^3$ and $R^4$ are each independently hydrogen or a $C_1$–$C_4$ alkyl group;

or a pharmnaceutically acceptable salt thereof.

2. A compound according to claim 1, wherein $R^1$ is F, Cl, Br, or I.

3. A compound according to claim 1, wherein $R^1$ is $CH_2X$, $CHX_2$, or $CX_3$, where X is F, Cl, Br, or I.

4. A compound according to claim 1, wherein $R^1$ is $CX_3$, where X is F, Cl, Br, or I.

5. A compound according to claim 1, wherein $R^1$ is $CCl_3$.

6. A compound according to claim 1, wherein $R^2$ is a fused aromatic ring.

7. A compound according to claim 1, wherein $R^2$ is a benzene or naphthalene ring.

8. A compound according to claim 7, wherein said benzene or naphthalene ring is substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, $SO_2NR^3R^4$ in which $R^3$ and $R^4$ are as defined above, and $SO_2F$.

9. A compound according to claim 8, wherein $R^2$ is a benzene ring.

10. A compound according to claim 9, wherein the benzene ring is substituted by one or more groups selected from halo, hydroxy, $C_1$–$C_4$ alkoxy or trifluoromethyl.

11. A compound according to claim 1 having the formula

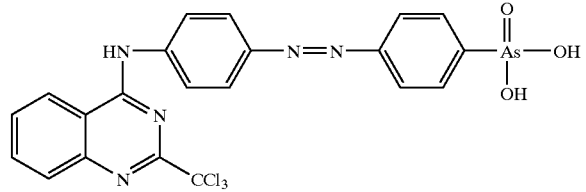

12. A method of inhibiting the growth of leukemia cells in a subject comprising administering to said subject a compound according to claim 1.

13. A method of inhibiting the growth of leukemia cells in a subject comprising administering to said subject a compound according to claim 11.

14. A method of treating leukemia comprising administering to said subject a compound according to claim 1.

15. A method of treating leukemia comprising administering to said subject a compound according to claim 11.

16. A pharmaceutical composition comprising:
   an amount of a compound according to claim 1 that is effective to inhibit leukemia cells; and
   at least one pharmaceutically acceptable carrier.

17. A pharmaceutical composition comprising:
   an amount of a compound according to claim 1 that is effective to treat leukemia; and
   at least one pharmaceutically acceptable carrier.

* * * * *

UNITED STATES PATENT AND TRADEMARK OFFICE
CERTIFICATE OF CORRECTION

PATENT NO. : 6,686,344 B1
DATED : February 3, 2004
INVENTOR(S) : Uckun

It is certified that error appears in the above-identified patent and that said Letters Patent is hereby corrected as shown below:

Title page,
Item [73], Assignee, "Paker Hughes Institute," should read -- Parker Hughes Institute --

Column 1,
Line 40, after the formula, insert -- $R^1$ is halo, or haloalkyl; --

Signed and Sealed this

Twenty-second Day of June, 2004

JON W. DUDAS
*Acting Director of the United States Patent and Trademark Office*